United States Patent [19]

Dick et al.

[11] Patent Number: 5,175,596
[45] Date of Patent: Dec. 29, 1992

[54] LIQUID NEPHELOMETER

[75] Inventors: Scott M. Dick, Alta Loma; Edward F. Patterson, Redlands; Gerhard Kreikebaum, San Bernadino, all of Calif.

[73] Assignee: Venturedyne, Ltd., West Allis, Wis.

[21] Appl. No.: 601,888

[22] Filed: Oct. 23, 1990

[51] Int. Cl.$^5$ .................. G01N 21/03; G01N 21/53
[52] U.S. Cl. ........................... 356/442; 356/339; 250/574
[58] Field of Search ............... 356/440, 441, 442, 246, 356/133, 338, 336, 339, 341, 342, 343; 250/574, 576

[56] References Cited

U.S. PATENT DOCUMENTS

| | | | |
|---|---|---|---|
| 4,591,268 | 5/1986 | Lew | 356/338 |
| 4,906,101 | 3/1990 | Lin et al. | 356/442 |

FOREIGN PATENT DOCUMENTS 0189439  8/1986  Japan .................. 356/246

*Primary Examiner*—Vincent P. McGraw
*Assistant Examiner*—LaCharles P. Keesee, II
*Attorney, Agent, or Firm*—Michael, Best & Friedrich

[57] ABSTRACT

The liquid nephelometer has an elongate, tubular housing for containing a liquid sample to be measured for the concentration of foreign materials, a light source located adjacent one or both ends of the housing for directing a beam of light along an axial path through the housing, a light restrictor having a aperture of reduced cross sectional area to divide the interior of the housing into a first or sensing chamber having a known volume and a second chamber and to limit the passage of the scattered light between the two chambers, and light detecting means for detecting light scattered by foreign material in the liquid present in one or both of the chambers and producing a signal representative of the concentration of such foreign material. In a preferred embodiment, the light source is located at the end of the housing including the sensing chamber, the portion of the housing including the second chamber is made from or coated with a light absorbing material and the light detector is disposed between the light source and the end of the sensing chamber, has a central opening through which the light beam passes and detects light back scattered by foreign material present in the liquid in the sensing chamber.

11 Claims, 2 Drawing Sheets

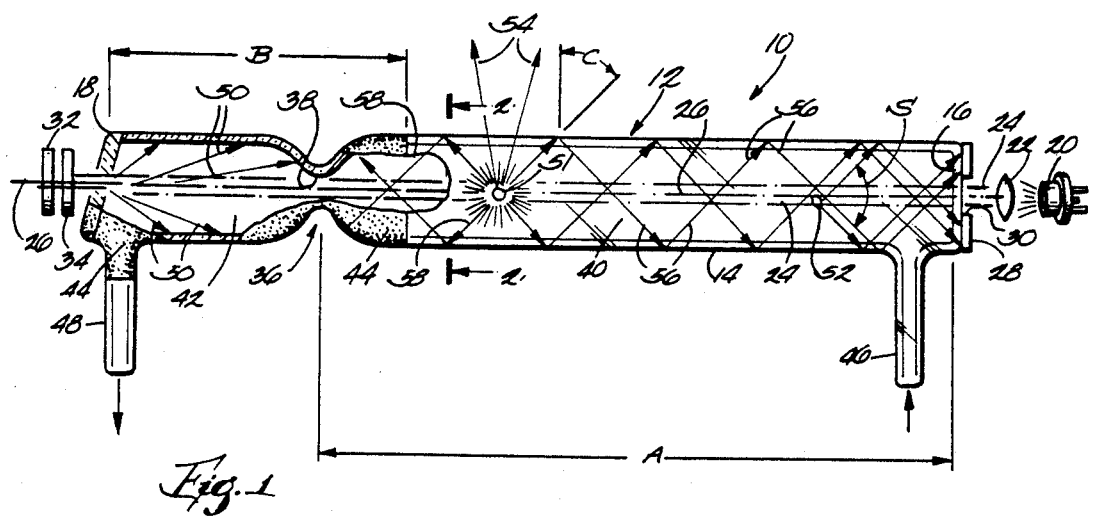
Fig. 1
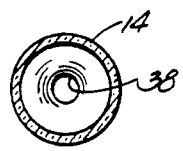
Fig. 2
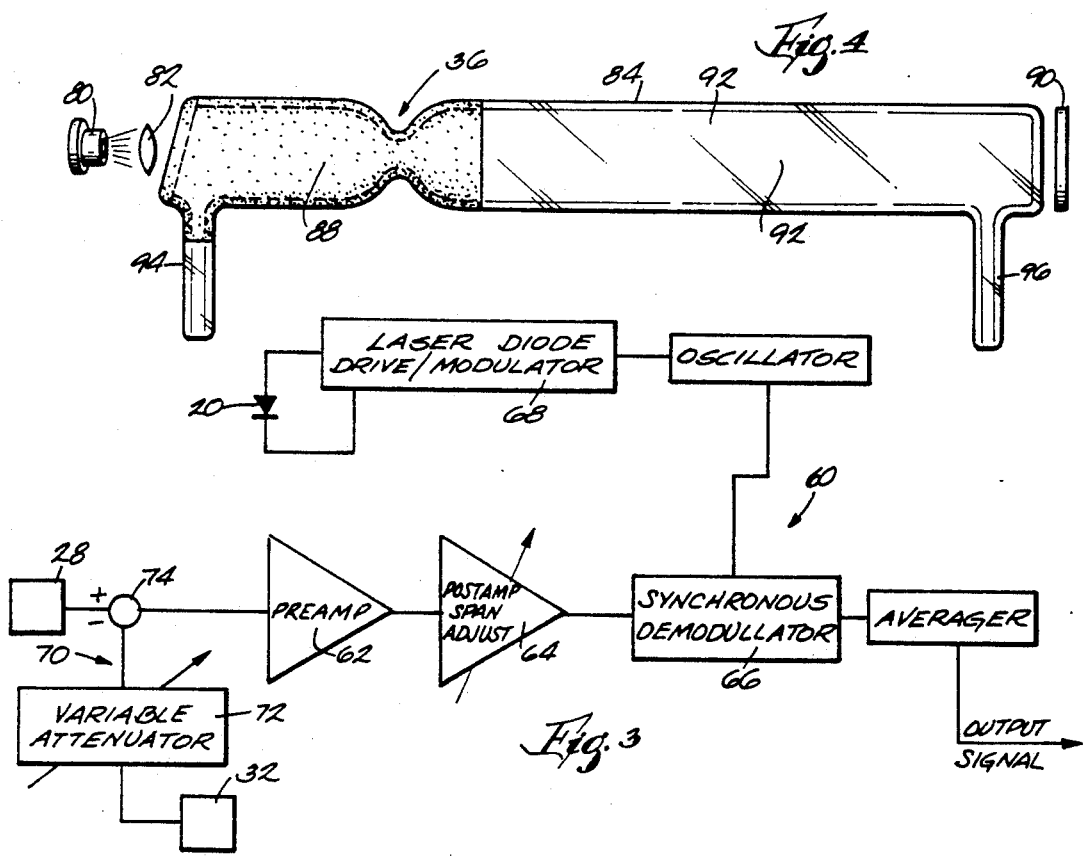
Fig. 4
Fig. 3

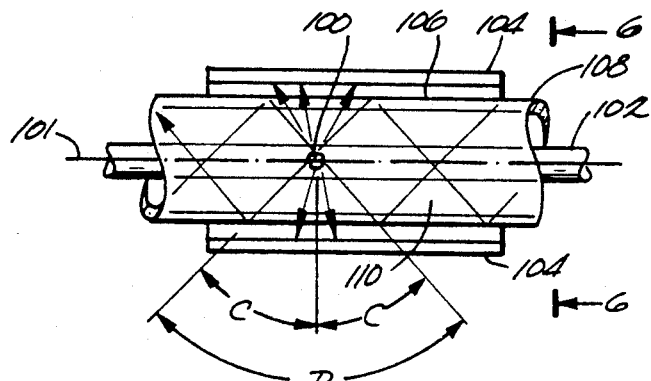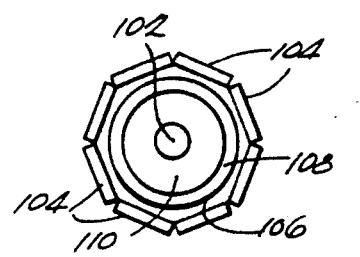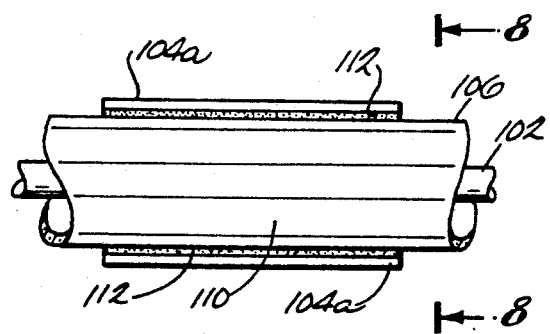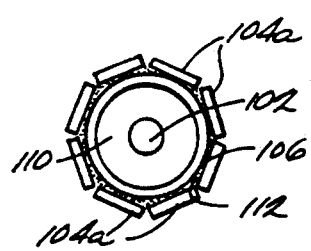

LIQUID NEPHELOMETER

BACKGROUND OF THE INVENTION

This invention relates to devices for measuring the concentration of contaminants or foreign materials in a fluid and, more particularly, to nephelometers for measuring the concentration of particulate materials in liquids.

A nephelometer generally is an optical instrument for measuring the concentration of particular contamination in a fluid, usually air. It does so by measuring the intensity of light scattered by clouds of particles in a known volume of the fluid being measured. Turbidity meters are commonly used to measure the quality of liquids, particularly water. They do so by measuring the attenuation of transmitted light through a solution containing finely divided particles in suspension. There is a direct relationship between the amount of light attenuated and the amount of material in suspension.

A nephelometer normally is calibrated in micrograms per cubic meter with a minimum response in the order of one microgram per cubic meter. A turbidity meter is calibrated in Nephelometric Turbidity Units (NTU). A nephelometer has greater sensitivity, accuracy and provision in measuring small amounts of turbidity. For example, the minimum response of higher grade turbidity meters is in the order of 0.01 NTU which is equivalent to approximately 30 milligrams per cubic meter. The sensitivity of both type instruments is limited by the light scatter collection angle (defined by the numerical aperture of the optical collection system), by the size of the viewing volume (defined by the optical depth of focus) and by the background stray light level inherent in the sensor.

SUMMARY OF THE INVENTION

The object of the invention is to provide a simply constructed liquid nephelometer having a minimum response substantially lower than that for conventional turbidity meters.

Another object of the invention is to provide a liquid nephelometer capable of providing a substantially uniform and predictable response to contaminants within a sensing chamber.

A further object of the invention is to provide a liquid nephelometer which determines the concentration of contaminants in a fluid by detecting the light scattered by particles in a fluid within a spherical angle.

Other objects, advantages and aspects of the invention will become apparent to those skilled in the art upon reviewing the following detailed description, the drawings and the appended claims.

The liquid nephelometer provided by the invention includes an elongate, tubular housing for containing a liquid sample to be measured for the concentration of foreign material, a light source located adjacent one or both ends of the housing for directing a beam of light along an axial path or optical axis through the housing and light restricting means including an aperture of reduced cross sectional area disposed in the housing between the opposite ends thereof with the aperture located coaxially with the axial path. The light restricting means divides the interior of the housing into a first chamber having a known volume and a second chamber and the aperture thereof limits the passage of scattered light between the first and second chambers. A light detecting means detects light scattered by foreign material in the liquid present in one or both of the chambers and produces a signal representative of the concentration of such foreign material.

In one embodiment, the first chamber serves as a sensing chamber having a known volume, the light source is located adjacent the end of the housing including the sensing chamber, at least the portion of the housing forming the sensing chamber is constructed from an optically transparent material, the portion of the housing forming the second chamber except for the end thereof, is made from or coated with a light absorbing material and the light detecting means is disposed between the light source and the end of the housing including the sensing chamber. The light detecting chamber has a central window through which the light beam passes and the light detecting means detects the light back-scattered by foreign material in the liquid present in the sensing chamber.

In another embodiment, the liquid nephelometer includes a light absorbing filter located adjacent the end of the housing including the second chamber for absorbing most, but not all, of the light impacting that end of the housing and also includes a light detecting means for detecting light leaking through the light absorbing filter.

In another embodiment, the light source is located adjacent the end of the housing including the second chamber, the first chamber has known volume and serves as sensing chamber, the light restricting means is located so that the volume of the second chamber is smaller than that of the sensing chamber, the portion of the housing forming the second end, except for a central window in thereof through which the light beam from the light sources passes, is made from or coated with a light absorbing material and the light detecting means is located adjacent the end of the housing including the sensing chamber and detects the light forward scattered by the foreign material in the liquid present in the sensing chamber.

BRIEF DESCRIPTION OF THE DRAWINGS

FIG. 1 is a simplified sectional and partially diagramatic view of the sensing portion of a liquid nephelometer embodying the invention.

FIG. 2 is a sectional view taken generally along line 2—2 in FIG. 1.

FIG. 3 is a block diagram of the signal processing system for the liquid nephelometer.

FIG. 4 is a view similar to FIG. 1 illustrating an alternate arrangement for the sensing portion of the liquid nephelometer.

FIG. 5 is a partial view of the sensing portion including an alternate arrangement for the light detectors.

FIG. 6 is a sectional view taken generally along line 6—6 in FIG. 5.

FIG. 7 is a view similar to FIG. 5 illustrating another alternate arrangement of the light detectors.

FIG. 8 is a section view taken generally along line 8—8 in FIG. 7.

DESCRIPTION OF THE PREFERRED EMBODIMENTS

While liquid nephelometers embodying the invention can be used to measure a concentration of a variety of foreign materials in a variety of different liquids, it is particularly adaptable for use in measuring very small solid particles in water and will be described in connection with such an application. It also can be adapted for other applications such as qualitative analysis (e.g., colorimetry) and spectroscopy.

Referring to FIGS. 1 and 2, the liquid nephelometer 10 has a sensing portion 12 including an elongate, tubular cell or housing 14 for containing a water sample to be measured for contamination and having windows 16 and 18 on the opposite ends which are at least partially optically transparent. While other suitable materials and configurations can be used, the sensing portion 12 preferably is cylindrical, has a circular cross section and is made from an optically transparent material, such as glass.

Suitably supported at one end of the housing 14 are a suitable light source 20 and beam shaping means 22 for directing a beam 24 of broadband or monochromatic light through the window 16 and toward the window 18 along an optical axis corresponding to the longitudinal axis 26 of the housing 12. A light detector 28 is disposed between the window 16 and the beam shaping means 22 and includes a central aperture 30 or transparent area which is coaxial with the optical axis 26 and through which the light beam 24 passes. Suitably supported at the other end of the housing 14 are a light detector 32 and a light absorbing filter 34. The filter does not absorb all of the light impinging on it and, instead, allows a small percentage to leak through to the light detector 32 which is used to control and maintain a stable baseline signal in a signal processing system as described below.

While the windows 16 and 18 can be flat with parallel surfaces or one or both surfaces of each can be curved or wedged shaped, in the specific construction illustrated, the surfaces of the window 16 are flat, parallel to each other and extend at a right angle to the optical axis 26 and the surfaces of the window 18 are flat, parallel to each other and extend at an acute angle to the optical axis 26 (i.e., are inclined relative to the optical axis 26).

The housing 14 also includes a light beam restrictor 36 disposed between the windows 16 and 18 and having a central aperture 38 of reduced cross sectional area which is located coaxially with the optical axis 26. The light beam restrictor 36 can be formed as an integral part of the housing 14 or fabricated separately and mechanically positioned inside the housing 14.

The light beam restrictor 36 divides the interior of the housing 14 into a sensing chamber 40 and a light absorbing chamber 42. The sensing chamber 40 has an effective sensing volume determined by the distance A between the window 16 and the center of the light beam restrictor aperture 38. The light absorbing chamber 42 includes a portion B of the housing 14, which preferably has a volume smaller than that of the sensing chamber 40. The portion B of the housing 14 extending from the outer edge of the angled window 18 to a location upstream of the light beam restrictor aperture 38 and excluding the angled window 18 is coated with a light absorbing material 44, such as black paint.

A liquid sample to be measured for contamination, such as process water used in the manufacture of semiconductors, is introduced into the sensing chamber 40 through an inlet port 46 located near the window 16 and, when continuous measurements are desired, is withdrawn from the light absorbing chamber 42 through an outlet port 48 located near the angled window 18.

The light source 20 preferably is a laser diode for emitting monochromatic light which is shaped by the beam shaping means 22 into the light beam 24. The light beam 24 is directed along the optical axis 26 through the aperture 30 in the light detector 28, the window 16, the light beam restrictor aperture 38 and the angled window 18 to the light filter 34. As mentioned above, a small amount of the light energy impacting the light filter 34 reaches the light detector 32. The angled window 18 directs incident light, represented by arrows 50, onto the walls of the light absorbing chamber 42 where it is absorbed. The light beam restrictor aperture 38 minimizes the effect of light scattered from the angled window 18 on the light detector 28 by functioning as an optical aperture between the angled window 18 and the light detector 28. Any scattered light outside the diameter of the light beam restrictor aperture 38 is absorbed by the walls of the light absorbing chamber 42 downstream of the light restrictor aperture 38.

Light rays scattered by foreign material anywhere in the sensing chamber 40, such as particles 51 and 52, either pass through the transparent walls of the sensing chamber 40 as illustrated by arrows 54, are reflected toward the light detector 28 as illustrated by arrows 56 or are reflected toward the light absorbing chamber 44 as illustrated by arrows 58 where it is absorbed. The sensing portion 12 of the nephelometer 10 usually is surrounded by air. The reflected rays are those that exceed a "critical angle" C with respect to the outside surface of the sensing chamber 40. This critical angle is defined by well known principles of physics and need not be described in detail, other than to state that in the preferred embodiment it is determined by the index of refraction of the liquid being measured.

Thus, some of the rays scattered by the particles 51 and 52 impact the light detector 28 directly. Others impact the light detector 28 after only one reflection off the walls of the sensing chamber 40 and still others impact the light detector 28 after multiple reflections off the walls of the sensing chamber 40. All of the scattered light energy from each particle 51 and 52 within a spherical angle S, defined by the critical angle of the liquid being measured less the angle of scatter subtended by the light detector aperture 30, is transmitted to the light detector 28.

If the index of refraction of the liquid being measured is greater than that of the surrounding air or other medium, then the sensing portion 12 of the liquid nephelometer 10, through the phenomena of total internal reflection, functions as its own light pipe type collector. The effective depth of focus of the light pipe is the length of the sensing chamber 40. The entire illuminated volume of the liquid in the sensing chamber 40 is monitored for contamination and the response to contamination at any location within this volume is uniform and predictable.

When the index of refraction of the fluid to be analyzed is less than that of the medium surrounding the sensing portion 12 of the liquid nephelometer 10, the inside or outside surface of the sensing chamber 40 can be coated with a light reflective material.

The liquid nephelometer 10 includes a suitable electronic signal processing system capable of producing an electronic signal representative of the contaminant concentration in the water being measured. FIG. 3 illustrates a preferred signal processing system 60 in which the light source 20 is a laser diode for emitting a monochromatic light. The laser diode 20 is modulated and the signal from the light detector 28, after being amplified in a conventional high gain detector/preamplifier circuit, represented diagramatically by 62 and 64, is synchronously demodulated in a suitable demodulation circuit 66. This makes the readings produced by the liquid nephelometer 10 relatively insensitive to moderate amounts of ambient light and light pick up and also makes the liquid nephelometer 10 insensitive to DC drift in the high gain detector/preamplifier circuit prior to synchronous demodulation.

In the specific embodiment illustrated, modulation of the laser diode 20 is accomplished electronically in a suitable laser diode drive/modulator circuit 68, preferably arranged to produce a 100% square modulation. Alternatively, modulation of the laser diode 20 and other light sources, such as gas lasers or white light sources, can be accomplished mechanically by a rotating chopper wheel or the like.

The light detector 28 also detects residual light in particle-free fluids originating from molecular scattering from the fluid and from stray light sources. This residual or background light cannot be distinguished from a contamination or turbidity signal. However, it is proportioned to the light intensity inside the sensing chamber 40. The signal processing system 60 includes a background light subtraction circuit 70 to compensate for this.

The background light subtraction circuit 70 includes the light detector 32, which serves as a reference, a variable attenuation circuit 72 and a suitable subtraction circuit 74. To obtain a zero turbidity reading with a particle-free fluid, the light intensity is monitored by the light detector 32 and its attenuated signal is subtracted from the signal from the light detector 28. Any changes in the background light level related to light intensity changes are compensated for. There is a compensation for light source drifting and aging, as well as for transmission changes in the entrance window 16 and the exit window 18. Inputting the signal from the reference detector 32 at the front end of the signal processing sequence insures that any electronic component drift in the sequence prior to synchronous demodulation does not affect the null reading.

Liquid nephelometers arranged in the manner illustrated in FIGS. 1-3 and described above have demonstrated a minimum response of 0.00002 NTU or 60 micrograms per cubic meter. Such a response approaches the performance of good grade airborne nephelometers. This is capability is highly advantageous, particularly in view of the simple, and therefore relatively inexpensive, construction and the reliability of liquid nephelometers embodying the invention.

In the embodiment illustrated in FIGS. 1-3, the liquid nephelometer 10 measures the total back-scattered light from contamination in the water being measured. FIG. 4 illustrates an alternate embodiment in which the total forward-scattered light is measured.

Referring to FIG. 4, the light source 80 and beam shaping means 82 are located at the end of the housing 84 closest to the light beam restrictor 36 and including the light absorbing chamber 88. The light detector 90 is located at the opposite end of the housing including the sensing chamber 92. The liquid sample to be measured can be introduced into the light absorbing chamber 88 through a first port 94 and is withdraw from the sensing chamber 92 through a second port 96 or vice versa.

FIGS. 5 and 6 illustrate an alternate arrangement of the light detector in which light scattered by a particle 100 radially outwardly relative to the optical axis 101 is collected at a nominal right angle D to the light beam 102 which is twice the critical angle C. A plurality of light detectors 104 are positioned as an array around the outer surface 106 of portion of the housing 108 defining the sensing chamber 110. The light detectors 104 are spaced radially outwardly from the outer surface 106 of the sensing chamber 110. Light scattered from contamination in the sensing chamber 110 which does not exceed the critical angle is measured by the light detectors 104. Such an arrangement can be used with back-scattered or forward-scattered measuring versions of the liquid nephelometer.

FIGS. 7 and 8 illustrate a light detector arrangement similar to that illustrated in FIGS. 5 and 6, except that the detectors 104a are positioned in an array around the outer surface 106 of the sensing chamber 110 and bonded directly to the outer surface 106 by a suitable optical bonding material 112.

In this embodiment, a critical angle does not exist because the bonding material 112 has the same or higher index of refraction as the fluid sample. Scattered light collection is a complete sphere, less the two cones of scatter subtended by the ends of the detector shell.

The liquid nephelometer can be arranged to respond to both forward and back scattering from contaminants by positioning a light source and an apertured light detector at each end of the housing and locating the light beam restrictor aperture at the center of the housing.

While preferred embodiments of the invention have been illustrated and described in detail, it will become apparent to those skilled in the art that various alterations and modifications can be made thereto without departing from the spirit and scope of the invention.

We claim:

1. A liquid nephelometer comprising
   housing for containing a liquid
   an elongate, tubular to be measured for the concentration of foreign material, said housing having first and second ends and at least a portion of each said first and second ends being optically transparent;
   a light source located adjacent one of said first and second ends for directing a beam of light along an axial path through said housing;
   light restricting means including an aperture of reduced cross sectional area disposed in said housing between said first and second ends with said aperture located coaxially with said axial path, said light restricting means dividing the interior of said housing into a first chamber including said first end of said housing and having a known volume and a second chamber including said second end of said housing, whereby said aperture limits the passage of scattered light between said first and second chambers;
   means for introducing a liquid sample into said first chamber; and
   light detecting means for detecting light scattered by foreign material in the liquid present in one of said first and second chambers and producing a signal representative of the concentration of such foreign material.

2. A liquid nephelometer according to claim 1 wherein
   said first chamber has said known volume and serves as a sensing chamber;
   said light restricting means is located closer to said second end of said housing;

said light source is located adjacent said first end of said housing;

the portion of said housing forming said second chamber, except for said second end, is made from or coated with a light absorbing material;

at least the portion of said housing forming said first chamber is constructed from an optically transparent material; and said light detecting means is disposed between said light source and said first end of said housing and includes a central opening through which the light beam from said light source passes, whereby said light detecting means detects the light back scattered by foreign material in the liquid present in said first chamber.

3. A liquid nephelometer according to claim 2 including means for withdrawing the liquid sample from said second chamber.

4. A liquid nephelometer according to claim 2 including light absorbing filter means located adjacent said second end of said housing for absorbing most, but not all, of the light impacting said second end of said housing; and light detecting means for detecting light leaking through said light absorbing filter means.

5. A liquid nephelometer according to claim 2 wherein the portion of said housing forming said first chamber, except for said first end, is coated with a light reflecting material.

6. A liquid nephelometer according to claim 2 wherein the inside surface of said second end of said housing extends in a plane which is inclined relative to said axial path.

7. A liquid nephelometer according to claim 1 wherein said housing is cylindrical;

at least the portion of said housing forming said first chamber is constructed from an optically transparent material;

the portion of said housing forming said second chamber is made from or coated with a light absorbing material;

said first chamber has said known volume and an outer surface; and said light detecting means comprises a plurality of light detectors disposed in an array around and spaced from the outer surface of said first chamber to detect light scattered by foreign material in the liquid present in said first chamber in a direction radially outwardly to said axial path and within a spherical angle which is twice the critical angle of the liquid present in said first chamber.

8. A liquid nephelometer according to claim 7 wherein said light detectors are bonded to the outer surface of said first chamber with a material having an index of refraction substantially equal to or greater than the index of refraction of the liquid.

9. A liquid nephelometer according to claim 1 wherein said light source is located adjacent said second end of said housing;

said first chamber has said known volume and serves as a sensing chamber;

said light restricting means is located closer to said second end of said housing than to said first end of said housing such that the volume of said second chamber is smaller than that of said first chamber;

the portion of said housing forming said second chamber, except for a central window in said second end through which the light beam from said light source passes, is made from or coated with a light absorbing material; and said light detecting means is located adjacent said first end of said housing and detects the light forward scattered by foreign material in the liquid present in said first chamber.

10. A liquid nephelometer according to claim 9 wherein at least the portion of said housing forming said first chamber is constructed from an optically transparent material.

11. A liquid nephelometer according to claim 10 wherein the portion of said housing forming said first chamber, except for said first end, is coated with a light reflecting material.

* * * * *

UNITED STATES PATENT AND TRADEMARK OFFICE
CERTIFICATE OF CORRECTION

PATENT NO. : 5,175,596
DATED : December 29, 1992
INVENTOR(S) : Scott M. Dick, Edward F. Patterson, and Gerhard Kreikebaum It is certified that error appears in the above-identified patent and that said Letters Patent is hereby corrected as shown below:

Claim 1, column 6, line 36, "housing for containing a liquid" should be deleted; and Claim 1, column 6, line 37, after "tubular" and before "to" --housing for containing a liquid-- should be inserted.

Signed and Sealed this

Twenty-sixth Day of October, 1993

Attest:

BRUCE LEHMAN

Attesting Officer    Commissioner of Patents and Trademarks